(12) United States Patent
Düring et al.

(10) Patent No.: US 10,758,316 B2
(45) Date of Patent: Sep. 1, 2020

(54) ROD-SHAPED BODY AND MEDICAL INSTRUMENT

(71) Applicant: MARVIS INTERVENTIONAL GMBH, Frechen (DE)

(72) Inventors: Klaus Düring, Frechen (DE); Nasib Dlaikan-Campos, Wurselen (DE); Maarten Van Dijk, Kaatsheuvel (NL)

(73) Assignee: MARVIS INTERVENTIONAL GMBH, Frechen (DE)

( * ) Notice: Subject to any disclaimer, the term of this patent is extended or adjusted under 35 U.S.C. 154(b) by 523 days.

(21) Appl. No.: 15/306,088

(22) PCT Filed: Apr. 23, 2015

(86) PCT No.: PCT/EP2015/000845
§ 371 (c)(1),
(2) Date: Oct. 22, 2016

(87) PCT Pub. No.: WO2015/161927
PCT Pub. Date: Oct. 29, 2015

(65) Prior Publication Data
US 2017/0042634 A1 Feb. 16, 2017

(30) Foreign Application Priority Data

Apr. 23, 2014 (DE) .................. 10 2014 005 777
Apr. 28, 2014 (DE) .................. 10 2014 005 994

(51) Int. Cl.
*A61B 90/00* (2016.01)
*A61L 31/18* (2006.01)
(Continued)

(52) U.S. Cl.
CPC .............. *A61B 90/39* (2016.02); *A61B 5/055* (2013.01); *A61L 31/022* (2013.01);
(Continued)

(58) Field of Classification Search
CPC ....... A61B 90/39; A61B 5/055; A61B 5/6851; A61B 2090/3954; A61M 25/09; A61M 25/0127; A61M 2025/09166
See application file for complete search history.

(56) References Cited

U.S. PATENT DOCUMENTS 4,257,421 A * 3/1981 Beal ................. A61M 25/09
600/434
5,154,179 A * 10/1992 Ratner .................. A61L 29/18
600/420
(Continued)

FOREIGN PATENT DOCUMENTS

WO    WO-2007000148 A2 * 1/2007 ........... A61L 31/026

OTHER PUBLICATIONS

DE102011081445, Uihlein, Bernhard, Medizinisches Fangdrahtinstrument, May 12, 2012 (2012).*
(Continued)

*Primary Examiner* — Sean P Dougherty
(74) *Attorney, Agent, or Firm* — Hultquist, PLLC; Steven J. Hultquist (57) ABSTRACT

The invention relates to a rod-shaped body comprising a central section and a peripheral section, wherein the central section is arranged in the center of the rod-shaped body and is enclosed by the peripheral section. Both the central section and the peripheral section substantially extend along the entire length of the rod-shaped body. The central section comprises at least one non-metallic fiber bundle that is embedded in a non-ferromagnetic matrix material. The matrix material is doped with marker particles. The peripheral section comprises at least one undoped, non-ferromagnetic matrix material. The diameter of the central section is less than or equal to 0.2 mm, preferably less than or equal
(Continued)

to 0.15 mm, and even more preferably, less than or equal to 0.1 mm, and in particular less than or equal to 0.08 mm.

19 Claims, 1 Drawing Sheet

(51) Int. Cl.
| | |
|---|---|
| *A61B 5/055* | (2006.01) |
| *A61L 31/02* | (2006.01) |
| *A61L 31/10* | (2006.01) |
| *A61L 31/14* | (2006.01) |
| *A61M 25/01* | (2006.01) |
| *A61M 25/09* | (2006.01) |
| *G01R 33/28* | (2006.01) |
| *A61B 5/00* | (2006.01) |

(52) U.S. Cl.
CPC .............. *A61L 31/026* (2013.01); *A61L 31/10* (2013.01); *A61L 31/14* (2013.01); *A61L 31/18* (2013.01); *A61M 25/0127* (2013.01); *A61M 25/09* (2013.01); *G01R 33/287* (2013.01); *A61B 5/6851* (2013.01); *A61B 2090/3954* (2016.02); *A61M 2025/09133* (2013.01); *A61M 2025/09166* (2013.01)

(56) References Cited

U.S. PATENT DOCUMENTS

| | | | | |
|---|---|---|---|---|
| 5,251,640 | A * | 10/1993 | Osborne | A61L 31/121 600/585 |
| 5,253,318 | A * | 10/1993 | Sayegh | G02B 6/4403 385/114 |
| 5,705,014 | A * | 1/1998 | Schenck | G01R 33/28 156/242 |
| 5,938,601 | A * | 8/1999 | Young | G01R 33/285 324/318 |
| 6,174,330 | B1 * | 1/2001 | Stinson | A61B 17/12022 606/198 |
| 6,574,497 | B1 * | 6/2003 | Pacetti | A61L 29/18 600/420 |
| 8,900,183 | B2 * | 12/2014 | Widdecke | A61M 25/0012 604/95.04 |
| 9,038,639 | B2 | 5/2015 | Pfeffer et al. | |
| 9,358,386 | B2 | 6/2016 | Duering | |
| 10,035,002 | B2 * | 7/2018 | Weiss | A61M 25/09 |
| 2003/0099764 | A1 | 5/2003 | Li et al. | |
| 2003/0208142 | A1 * | 11/2003 | Boudewijn | A61B 5/064 600/585 |
| 2004/0143180 | A1 * | 7/2004 | Zhong | A61K 49/1896 600/410 |
| 2006/0293581 | A1 * | 12/2006 | Plewes | A61K 49/0419 600/407 |
| 2008/0236869 | A1 * | 10/2008 | Marte | H01L 39/02 174/125.1 |
| 2010/0063379 | A1 * | 3/2010 | Pfeffer | A61L 29/126 600/410 |
| 2011/0166439 | A1 | 7/2011 | Pfeffer et al. | |
| 2013/0289533 | A1 | 10/2013 | Duering et al. | |
| 2013/0324837 | A1 * | 12/2013 | Meyer | A61L 29/085 600/417 |
| 2014/0018839 | A1 * | 1/2014 | Renner | A61F 5/08 606/199 |
| 2014/0221818 | A1 * | 8/2014 | Duering | A61N 1/05 600/411 |
| 2015/0190614 | A1 * | 7/2015 | Uihlein | A61M 25/09 600/417 |
| 2018/0361129 | A1 * | 12/2018 | Renner | A61M 29/02 |

OTHER PUBLICATIONS

EPO/Google Translation of DE102011081445, Uihlein, Bernhard, Medizinisches Fangdrahtinstrument, May 12, 2012 (2012).*

* cited by examiner

ROD-SHAPED BODY AND MEDICAL INSTRUMENT

CROSS-REFERENCE TO RELATED APPLICATIONS

This application is a U.S. national phase application under the provisions of 35 U.S.C. § 371 of International Patent Application No. PCT/EP15/00845 filed Apr. 23, 2015, which in turn claims priority of both European Patent Application No. 10 2014 005 777.1 filed Apr. 23, 2014, and European Patent Application No. 10 2014 005 994.4 filed Apr. 28, 2014. The disclosures of such international patent application and European priority patent applications are hereby incorporated herein by reference in their respective entireties, for all purposes.

The present invention relates to a rod-shaped body and a medical instrument. In particular, the present invention relates to a medical instrument which comprises at least one rod-shaped body, whereas the rod-shaped body or the medical instrument, resp., can be detected by means of magnetic resonance imaging.

WO 2007/000148 A2 discloses a rod-shaped body provided for the design of medical devices such as catheters or guidewires for catheters. This rod-shaped body consists of one or more filaments and a non-ferromagnetic matrix material, whereas the matrix material encloses the filaments. A doping made of particles which create artifacts in magnetic resonance imaging is embedded in the matrix material.

WO 2009/141165 A2 discloses a medical instrument which can be inserted into a human or animal body, wherein the medical instrument comprises an instrument body. The instrument body comprises at least one rod-shaped body having poor electrical conductivity and being formed from a matrix material and non-metallic filaments. This medical instrument is characterized in that the rod-shaped body is doped with an X-ray marker, and in that the medical instrument comprises an MR marker.

WO 2012/052159 A2 discloses a rod-shaped body and a medical instrument. The rod-shaped body comprises one or more non-metallic filaments and a non-ferromagnetic matrix material. The matrix material encloses and/or aggluntinates the filaments. The rod-shaped body comprises marker particles for generating a signal in magnetic resonance or X-ray imaging.

WO 2013/041235 A1 discloses a medical device which can be visualized by MRI during insertion or during positioning, resp., in the human and/or animal body and whose bending stiffness is modifiable. The medical device provides an elongated tubular lead probe and an elongated core which can be inserted into the lead probe, and which is made from non-metallic filaments and a matrix material.

A detailed explanation of magnetic resonance imaging (MRI) can be found in the Internet at http://en.wikipedia.org/wiki/MRT.

Such rod-shaped bodies are advantageous in that by embedding of one or more rod-shaped bodies in an envelope material a medical instrument can be provided, or that the rod-shaped bodies can be used as cores for lead probes in medical instruments. The rod-shaped bodies can comprise different doping materials. By using different types of rod-shaped bodies medical devices with different doping materials (=marker) can be produced. Thereby, they have different properties regarding their visibility in X-ray and magnetic resonance imaging. These various medical instruments can be manufactured by the same processes in the same production run, whereas only one or more rod-shaped bodies have to be exchanged. Thus it is possible to economically manufacture different types of medical instruments, even if these are produced only in small numbers.

One object of the present invention is to further improve such rod-shaped bodies.

Another object of the invention is to provide rod-shaped bodies which can be manufactured more easily and with improved quality.

Another object of the invention is to provide rod-shaped bodies with improved mechanical properties.

Another object of the invention is to provide improved medical instruments by an improved composition of the rod-shaped bodies, in particular MR compatible guidewires, which optimally exploit the properties of the rod-shaped bodies.

Another object is to provide improved rod-shaped bodies and medical instruments which lead to an improved visualization in magnetic resonance imaging and in particular a sharper and more confined MRI artifact.

Another object is to provide improved micro MR guidewires.

The invention comprises the features specified in the independent patent claims for solving these objects. Advantageous embodiments thereof are specified in the respective dependent claims.

According to a first aspect the rod-shaped body comprises a central section and a peripheral section, whereas the central section is arranged in the center of the rod-shaped body and enclosed by the peripheral section. The central section as well as the peripheral section extend substantially along the entire length of the rod-shaped body. The central section comprises at least one non-metallic fiber bundle embedded in a non-ferromagnetic matrix material. The matrix material is doped with marker particles. The peripheral section comprises an undoped non-ferromagnetic matrix material. The diameter of the central section is less than or equal to 0.2 mm, preferably less than or equal to 0.15 mm, and even more preferably less than or equal to 0.1 mm, and in particular less than or equal to 0.08 mm.

As only the matrix material of the very small central section is doped with MR marker particles a particularly narrow and sharp artifact is generated during magnetic resonance imaging.

Such a concentrated disposition of a lower amount of MR marker particles compared to the state of the art is advantageous compared to the one with a higher amount of MR marker particles which are distributed in the whole rod-shaped body, because the voxels along the concentrated disposition of MR particles are blackened but these voxels provide the same level of blackening as with a higher amount of MR marker particles distributed over an accordingly larger range. Thereby in the width a lower number of voxels is blackened and a narrower image of the medical instrument is achieved so that less target tissue can be covered by blackening in the MRI image.

Therefore, with a rod-shaped body with MR marker doping only in the central section according to the present invention it is possible to generate an almost equally narrow image in MRI as with a metallic guidewires in X-ray imaging. This especially applies if the medical instrument has only one doped rod-shaped body or in case of several rod-shaped bodies only the centrally positioned rod-shaped body contains MR marker. Preferably then the rod-shaped body with central disposition of the marker particles is positioned in the center of the guidewire. Herewith the distance between the doped central section and the surface of the guidewire is kept maximal. This leads to that water or fat molecules in the body to be examined cannot get closer to the central section than only to the surface of the guidewire. Thereby the resonance between MR markers and water molecules is kept low whereby the artifacts generated by the MR markers are narrow and the guidewire represents itself as a narrow line in MR imaging.

Moreover, it has turned out that due to the concentration of the MR marker in the central section the amount of MR marker in the matrix material can vary over a broad range without significant influence on the representation of the guidewire in MR imaging. When using iron particles with a particle size of 0 to 20 µm in a weight/weight-ratio of ca. 1:5 to 1:30 (marker : matrix material) substantially the same representation has been achieved. It became evident that the local concentration in an as small as possible region, i.e. the central section, has much more influence on the representation in MR imaging than the amount of markers in the matrix material.

The rod-shaped body preferably has a diameter of not more than 0.75 mm, and in particular a diameter of 0.5 mm. With this invention for the first time thin rod-shaped bodies with a structure providing a central section and a peripheral section are created.

A rod-shaped body is a single-piece solid material body. It is not a tubular hollow body.

Preferably the rod-shaped body consists of a homogeneous matrix material. The matrix material of the peripheral section and of the central section therefore consist of the same material type. The preferred material type is epoxy resin. Other material types can be provided from other, preferably also chemically reactive and functional polymers. Appropriate examples are radicalic or ionic cross-linkings of polymers, such as e.g. of unsaturated polyesters, etherifications and esterifications of polysaccharides, hydrolysis of polyvinylesters or acetalization of polyvinyl alcohol.

Preferably the non-metallic fibers in the peripheral section are provided about equally distributed relative to the cross-section. Thereby a high torsional and bending stiffness is achieved also in a thin or small-volume peripheral section.

It has turned out that by concentration in the central section the total amount of MR marker is very low and nevertheless a very good representation is achieved.

In this way the best possible representation of a medical instrument, in particular a guidewire which comprises such a rod-shaped body with doping only in the central section, is achieved.

In addition to the MR marker particles contained in the central section of the rod-shaped body a separate MR tip marker can be applied to the distal end section of the medical instruments which generates in the MR image a wider artifact, e.g. with the double to triple width compared to the artifact over the entire length of the medical instrument. With such a tip marker the tip of the medical instrument and thereby its very distal end can unequivocally be determined in the MR image. If the tip marker is not visible in the MR image then the tip is not present in the visualized slice of the MRI recording and the slice must be adjusted.

The MR tip marker can by example be prepared by applying a self-hardening polymer solution which contains MR marker particles. After hardening the polymer solution forms a layer which preferably extends over a longitudinal region of some pm to some mm. This layer may only be applied to one front surface of the rod-shaped body so that the longitudinal extension corresponds to the thickness of the layer. Yet, this layer may also be applied to the lateral surface of the rod-shaped body whereas the longitudinal extension in that case preferably is not longer than 5 mm and in particular not longer than 3 mm. The polymer solution can consist e.g. of PEBAX or a glue. All MR marker particles disclosed herein can be applied as MR marker particles whereas iron particles are preferred. The tip marker can be covered by additional layers such as e.g. an envelope material layer. Preferred is such an additional covering with a polymer material.

At the distal end of the medical instrument also several tip markers may be applied, preferably in a defined distance to each other. In this way a measuring function may be integrated into the medical instrument for measuring the length of e.g. a vessel stenosis in the body.

The size and especially the width of the tip marker artifact is dependent from the absolute amount of MR marker particles applied, and from the layer thickness of the material/polymer layer being present on top of the tip marker as this determines the distance to the surrounding water or fat molecules.

A fiber bundle may comprise at least one elongated or several elongated fibers and preferably several elongated fibers which are arranged in parallel or interlaced with each other or twisted. Due to that the fiber bundles comprise at least one elongated or several elongated fibers the fiber bundle provides a high stability in longitudinal direction to the rod-shaped bodies. By such a structured formation and arrangement of the fiber bundles in the rod-shaped bodies an improved product quality is achieved.

The fiber bundle in the central section can be an ht-fiber bundle and the fiber bundle in the peripheral section can be a glass fiber bundle.

An ht-fiber bundle is a high-tenacity fiber bundle. Typical examples for ht-fiber bundles are aramid fibers and UHMWPE fibers (Ultra High Molecular Weight Polyethylene fibers). ht-fiber bundles have a tensile or tearing strength, resp., of at least 20 cN/tex. Optionally the ht-fiber bundles have a tensile or tearing strength, resp., of at least 32 cN/tex and in particular of at least 30 cN/tex.

An ht-fiber bundle is highly flexible or bendable and provides a high tensile or tearing strength, resp. In this way it is ensured that even if the rod-shaped body should break in the human or animal body during the medical intervention the broken parts still remain connected with each other by the ht-fiber bundle and, thereby, the medical instrument is safely removable. Moreover, the ht-fiber bundle embedded in the matrix material provides a certain stiffness to the rod-shaped body.

Glass fiber bundles are stiffer than ht-fiber bundles so that a medical instrument which comprises ht-fiber bundles as well as glass fiber bundles is preferred.

A rod-shaped body comprising ht-fiber bundles as well as glass fiber bundles can be optimally adjusted in terms of stiffness and flexibility and particularly torsional stiffness.

The arrangement of at least one glass fiber bundle in the peripheral section enables the highest possible stiffness. The at least one peripheral glass fiber bundle provides the necessary compression and bending stiffness to the rod-shaped body. By arranging at least one ht-fiber bundle centrally on a neutral line this one ht-fiber bundle only minimally reduces the compression and bending stiffness of the rod-shaped body. In the technical mechanics, specifically in elastostatics, a neutral line, also called zero line, is defined as the layer of a cross-section of a rod-shaped body whose length does not change during a bending process. Bending does not cause tensile or compressive stress at this position. The area runs through the geometric center of the cross-section area of the rod-shaped body.

The at least one fiber bundle in the central section can also be a glass fiber bundle and the at least one fiber bundle in the peripheral section can also be an ht-fiber bundle. This arrangement is optimal when the rod-shaped body shall have a low amount of glass fibers and a high amount of ht-fibers. In this embodiment a rod-shaped body predominantly consisting of the more flexible ht-fibers is reinforced by the glass fibers in its compression and bending stiffness.

It is advantageous to arrange at the surface of the rod-shaped body the fibers contained in the higher amount and inside those contained in the lower amount in order to obtain a homogeneous surface. Product quality in this way is significantly enhanced.

The non-metallic fiber bundles are electrically non-conductive fibers or filaments, resp., so that these are applicable during magnetic resonance imaging. Hence, the term "non-metallic fiber bundle" as used in the present description excludes any electrically conductive fibers as e.g. thin metal wires or a carbon filament.

Preferably a fiber bundle is made from several fibers. Such a fiber bundle is English is called a "roving".

If the fibers of the fiber bundle are twisted they form a yarn. Such a fiber bundle in English is called a "yarn".

All fiber bundles in rod-shaped bodies may be ht-fiber bundles. In such an embodiment the rod-shaped body provides best possible properties regarding tearing strength.

Furthermore, all fiber bundles in a rod-shaped body may be glass fiber bundles. Such a rod-shaped body provides best possible properties regarding compression and bending strength.

The non-ferromagnetic matrix material in the central section and in the peripheral section may be the same non-ferromagnetic matrix material. A preferred matrix material is epoxy resin.

The marker particles in the central section preferably are MR marker particles.

In the central section one or more fiber bundles may be provided, and in the peripheral section radially circumferential around the fiber bundle of the central section and approximately equally distant from each other at least three, or four, or five, or six, or seven, or eight, or nine, or ten, or eleven, or twelve, resp., fiber bundles may be provided.

According to a second aspect of the present invention a medical instrument, e.g. a guidewire or a catheter or a core for a lead probe, in particular a micro guidewire, comprises a rod-shaped body according to the foregoing description.

Such a micro guidewire or such a core made from only one rod-shaped body achieves maximal bending and compression stiffness whereas tearing strength is ensured by the ht-fiber bundle.

By solely doping the matrix material of the central section of the rod-shaped body of the guidewire with MR marker particles a particularly narrow and sharp artifact is generated in MR imaging. Regarding the advantages of narrow artifacts it is referred to the explanations concerning the rod-shaped body according to the present invention.

In the region of the distal end forming the tip of a guidewire or core the amount of glass fibers of the fiber bundle may be smaller than in the other part of the guidewire.

Thereby such a micro guidewire or such a core provides a flexible tip at the distal end which is formed by having a smaller amount of glass fibers than in the residual part of the guidewire or the core, or that the amount is very low, or that there are no glass fibers, resp. Thereby the flexible tip preferably contains only ht-fibers or an ht-fiber matrix composite so that it is plastically deformable. This is desirable in clinical practice for a quick adaptation of the flexible tip to the vessel structures in a target region. The flexible tip can be formed to the desired shape by the physician himself, without needing hot steam and/or otherwise warming-up. Thus such a micro guidewire is highly flexibly usable and economically producible as no different shapes of tips need to be manufactured. Moreover, the plastic deformability allows a much better adaptation to the requirements of the applying physician.

If the amount of glass fibers, however, is substantially higher than that of the ht-fibers, such flexible tips can be formed by action of heat into a predefined shape not simply to be modified or be impinged with a desired bending radius.

A rod-shaped body for a micro guidewire comprises preferably in the central section one or two ht-fiber bundles and several glass fiber bundles in the peripheral section.

Furthermore, the micro guidewire can be enclosed by an envelope material, e.g. polyamide or polyurethane. The envelope material can also be provided e.g. by a shrink tube (preferably made from PTFE [Polytetrafluoroethylene] or FEP [Fluoroethylene-propylene]). A shrink tube improves the properties regarding tearing strength of the guidewire compared to an envelope material applied e.g. by extrusion.

By forming the surface with a material with lowest possible friction, e.g. PTFE, in addition the mechanical properties of the respective medical instrument are further improved. For example, guidewires made from fiber-reinforced polymers (FRP) usually do not have optimal torque properties compared to guidewires made from metal cores, due to the differing material properties. By providing the minimal friction at e.g. the wall of a blood vessel or a catheter wall resulting from a low-friction guidewire surface the mechanical requirements regarding the torque stability of such an FRP-based guidewire are lowered.

Concerning the micro guidewires it has to be noted that almost no distance between MR marker particles from the surrounding water or fat molecules can be realized if the entire rod-shaped body is doped. This means that the MR marker particles in micro guidewires known in the state of the art are arranged almost directly neighbouring the surrounding water or fat molecules. This leads to artifacts wider than desired as, unlike with standard or stiff guidewires which are composed of several rod-shaped bodies (see WO 2012/052159 A2), not only the central rod-shaped body can be doped, so that this one has a larger distance from the surrounding water or fat molecules.

A micro guidewire embodied according to the present invention, therefore, generates a very narrow and very sharp artifact as the MR marker particles in the rod-shaped body due to the concentrated central arrangement are sufficiently distant to the surrounding water or fat molecules and, thereby, only the minimally possible number of voxels is blackened.

According to another aspect of the present invention a guidewire comprises at least one central rod-shaped body doped with MR marker only in the central section according to the foregoing description and at least one peripheral rod-shaped body, whereas the central rod-shaped body is arranged in the center of the guidewire, and wherein the central rod-shaped body and the peripheral rod-shaped body extend substantially along the entire length of the guidewire. The peripheral rod-shaped body provides at least one non-metallic fiber bundle embedded in an undoped, non-ferromagnetic matrix material. The central rod-shaped body and the peripheral rod-shaped body are embedded in a non-ferromagnetic envelope material. In addition for increasing tearing strength and for achieving an optimally smooth surface a shrink tube can be applied.

Such a guidewire embodied according to the present invention thus generates a very narrow and very sharp artifact as the MR marker particles in the central rod-shaped body by their concentrated centered arrangement are optimally concentrated and optimally distant from surrounding water.

The central rod-shaped body may have a central section and a peripheral section, wherein the central section is arranged in the center of the rod-shaped body and enclosed by the peripheral section, whereas the central section as well as the peripheral section extend over the entire length of the rod-shaped body, and the central section provides at least one glass fiber bundle and the peripheral section provides at least one ht-fiber bundle, whereas both fiber bundles are embedded in a non-ferromagnetic matrix material.

The fiber bundle of the peripheral rod-shaped body may be a glass fiber bundle.

The peripheral rod-shaped body may have a central section and a peripheral section, whereas the central section is arranged in the center of the rod-shaped body and is encased by the peripheral section, whereas the central section as well as the peripheral section extend over the entire length of the rod-shaped body, and the central section provides at least one ht-fiber bundle and the peripheral section at least one glass fiber bundle, whereas both fiber bundles are embedded in a non-ferromagnetic matrix material.

The guidewire may have a central rod-shaped body and at least three, or four, or five, or six, or seven, or eight, or nine, or ten, or eleven, of twelve, resp., rod-shaped bodies.

According to another aspect of the present invention a method for manufacturing of a rod-shaped body according to the foregoing description is provided, wherein a central section of at least one non-metallic fiber bundle with a non-ferromagnetic matrix material doped with MR marker particles is provided, and on the central section by impregnation of at least one non-metallic fiber bundle with undoped non-ferromagnetic matrix material a peripheral section is provided so that the latter encloses the central section.

As in the embodiment of the rod-shaped bodies according to the present invention the MR marker particles are arranged inside of the rod-shaped body, these are not present at the surface of the rod-shaped body and do not impair the pultrusion process as it may happen if the MR marker particles are located at the surface of the rod-shaped bodies and, therefore, may lead to uneven passing across the die which can lead to inhomogeneities in the pultrudate. The more homogeneous the pultrusion process runs, the higher is the product quality.

The structured arrangement of the fibers, in particular if two ore more different types of fibers are comprised in one rod-shaped body, leads to a better and more homogeneous impregnation of the fibers with the matrix material and, therefore, to a higher product quality, too.

The arrangement of all ht-fibers comprised in a medical instrument in a single rod-shaped body gives it the best possible tearing strength and, thereby, an improved product quality.

The foregoing described various aspects of the present invention can be combined with each other.

The guidewire preferably is enclosed by a shrink tube, preferably made from PTFE (Polytetrafluoroethylene) or FEP (Fluoroethylene-propylene). This improves its properties regarding the tearing strength and creates an optimally smooth surface with minimal friction which further optimizes the torque properties of the guidewire.

The envelope material ordinarily provides a squatting temperature which is below 300° C. or below 250° C., resp. The shrink tube, however, shall be heatable to a temperature of above 250°, or above 300° C., e.g. 350° C., resp., in order to shrink and to closely attach to the guidewire. In case of heating with a heat fan above 300° C. the shrink tube encasing such a medical instrument there exists the risk that the envelope material of the guidewire softens and, due to the pressure exerted by the airflow generated by the fan, the medical instrument is flattened. As a consequence the necessary geometric arrangement and/or roundness of the guidewire is lost.

To avoid this problem a guidewire enclosed by a not yet shrinked shrink tube may be heated by a heating tube through which the unit of guidewire and shrink tube is passed along.

The heating tube typically has a length of 1 to 2 cm. The length of the heating tube may also be up to 3 cm, or up to 5 cm, or up to 10 cm, resp. The heating tube may also be provided as a short ring with a length of not less than 0.5 cm, or a length of not less than 0.7 cm, resp. The diameter of the heating tube is dimensioned such that therein the guidewire and the shrink tube can be arranged with a small distance to the inner surface of the heating tube. This distance is e.g. at least 1 mm, whereas it is preferably at least 3 mm, or 5 mm, resp. The heating tube typically has a diameter between 0.5 and 5 mm. The diameter preferably is 0.7 to 3 mm and in particular 0.8 to 2 cm. The heating tube preferably is a metal tube with good heat conductivity or a tube-like housing e.g. made from copper, brass, bronze, red brass, aluminum bronze, stannous bronze, copper-chromium(I)-zircon, copper-nickel, copper-aluminum, white copper, Ampcoloy®, other copper-containing or copper-based alloys or steel. Heating elements are provided at the outer surface or in the jacket of the heating tube. Moreover, the heating tube is provided with one or more temperature sensors for measuring the temperature of the heating tube and to be able to exactly set the temperature. As the guidewire enclosed by the shrink tube is guided with distance to the inner surface of the heating tube, the heat originating from the heating tube is transferred to the medical instrument via irradiation and convection. In order to ensure a sufficiently long dwell time of the medical instrument in the heating tube the speed for passing the medical instrument through the heating tube should not be higher than 5 m/min, preferably not higher than 2 m/min, or not higher than 1 m/min, and in particular not higher than 0.75 m/min, resp. To ensure that the envelope material of the shrink tube does not soften during shrinking of the shrink tube the speed with which the guidewire enclosed by a shrink tube is moved may be at least 1 m/min, and preferably at least 0.3 m/min, and in particular 0.5 m/min, resp. The actually required speed depends from the dimensions and the materials, especially the envelope material, of the guidewire and the thickness of the shrink tube and has to be determined individually for each case. The foregoing described heating via a heating tube enables the necessary fine tuning of the heat input into the shrink tube, which should be as high as possible, and into the guidewire, especially the envelope material, which should be as low as possible. By the ability to freely combine length and diameter of the heating tube with the process speed and the process temperature without exerting pressure onto the heated guidewire a gentle application of the shrink tube to the composite material is enabled.

The guidewire may be a micro guidewire which consists of a single rod-shaped body without envelope material. Preferably the guidewire is a guidewire consisting of one or more rod-shaped bodies which are embedded in an envelope material.

Such a medical instrument comprising a guidewire and a shrink tube constitutes an independent aspect of the present invention which can be realized independent from the aspects described above. This aspect obviously may also be embodied in connection with the above described aspects of the invention.

The invention will be explained below with the aid of the illustrations. These show in.

Some of the embodiments of the present invention are provided with aramid fiber bundles. In the following description of the present invention the terms "aramid fiber" and "aramid filaments" are used as a synonym for ht-fiber bundle. Aramid fibers are provided based on their high tensile and tearing strength. Therefore, the person skilled in the art understands that the aramid fibers may be exchanged by other electrically non-conductive fibers which exhibit almost equal or better tensile or tearing strength.

The first aspect of the present invention relates to a rod-shaped body 1 (in the following also called rod) which on the one hand represents an end product, e.g. a micro guidewire, but in particular an intermediate product for manufacturing of medical instruments, particularly guidewires or catheters or tube- or catheter-based instruments or cores for lead probes, resp.

The rod-shaped body according to the present invention is an advancement of the rod-shaped bodies as disclosed in WO 2007/000148 A2, WO 2009/141165 A2 and WO 2013/041235 A1. Therefore, reference is made to its full extent to the disclosures of these documents and these documents are included into the present disclosure by reference.

In the following a rod-shaped body according to the present invention is described in general.

Figure 1:
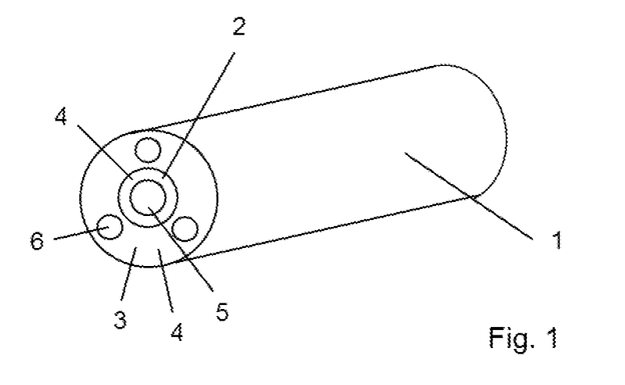
FIG. 1 a perspective view of a rod-shaped body according to the present invention, FIG. 2 the rod-shaped body of FIG. 1 in a cross-sectional view, and FIG. 3 a guidewire according to the present invention in a cross-sectional view.
Figure 2:
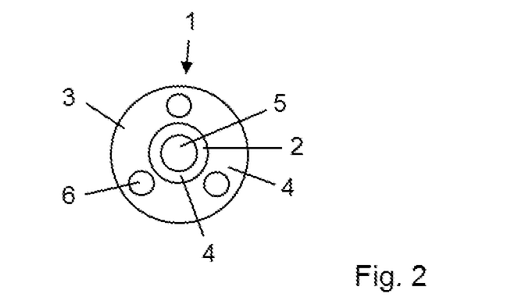

A rod-shaped body or rod 1 comprises a central section 2 and a peripheral section 3 (FIGS. 1 and 2). The central section 2 is arranged in the center of the rod 2 and enclosed by the peripheral section 3.

The central section 2 as well as the peripheral section 3 extend along the entire length of the rod-shaped body.

The central section 2 has at least one non-metallic fiber bundle 5 which is embedded in a non-ferromagnetic matrix material 4.

The fiber bundle 5 has a fineness of 11 Tex. The central section has a diameter of about 0.1-0.15 mm, in particular of maximally 0.15 mm, or maximally 0.1 mm, resp.

The matrix material in the central section is doped with MR marker particles (not shown). The peripheral section 3 has at least one non-metallic fiber bundle 6 which is embedded in a non-ferromagnetic matrix material 4.

The rod-shaped body has a diameter of less than 0.75 mm, or less than 0.5 m, or less than 0.3 mm, or less than 0.2 mm, or less than 0.1 mm, resp.

The non-metallic fiber bundles 5, 6 are electrically non-conductive fibers or filaments, resp. Electrically conductive fiber bundles would conduct electric voltage and the rod-shaped body 1 would heat up due to the magnetic and RF fields induced during magnetic resonance imaging.

The rod-shaped bodies 1 may comprise metallic particles, but these particles must be such distant from each other that they do not develop electrically conductive regions.

The matrix material encloses and/or agglutinates the fiber bundles in such a way that these are embedded therein. The non-ferromagnetic matrix material 4 of the central section 2 is doped with MR marker particles.

An essential feature and a key advantage of the rod-shaped body 1 is that different rod-shaped bodies may contain different doping with MR marker particles.

In a guidewire differently doped and/or undoped rod-shaped bodies may be integrated.

This will be described in more detail in the following by reference to the various embodiments of the rod-shaped bodies and the guidewires according to the present invention.

According to a first embodiment of the rod-shaped body 1 in the central section an aramid fiber bundle is embedded in the matrix material 4 which is doped with MR marker particles. The fiber bundle comprises several elongated fibers arranged in parallel. Alternatively, the fibers may also be twisted or interlaced with each other.

In the peripheral section 3 surrounding the central section 2 three glass fiber bundles are radially circumferential arranged equally distant from each other in the matrix material 4. The matrix material 4 in the peripheral section 3 is not doped. The glass fiber bundles preferably comprise several elongated fibers which are arranged in parallel.

Alternatively, these fibers of the glass fiber bundle may also be twisted with each other or interlaced.

"Elongated" in the context of the present invention means that the fiber bundles 5, 6 substantially extend along the entire length of the rod-shaped body 1. This means that the length of the fiber bundles 5, 6 is at least half of the length of the rod-shaped body 1. Preferably the fiber bundles 5, 6 extend along the entire length of the rod-shaped body 1 or along at least 80%, or along at least 90%, or along at least 95%, resp., of the entire length of the rod-shaped body 1.

Such elongated filaments provide to the rod-shaped body a high stability in longitudinal direction. Guidewires which comprise at least one such rod-shaped body are designed to be insertable into a blood vessel, an organ (e.g. heart, liver, lung or similar) or the brain. Therefore, a strong force can be applied to these guidewires in longitudinal direction during its insertion into the body lumen or during pulling out from the body lumen. This force is absorbed by the rod-shaped bodies 1.

Further, the guidewires must provide a certain flexibility in order to be steerable along curves in the body lumen. As the fiber bundles 5, 6 are arranged in longitudinal direction of the rod-shaped body, rod-shaped bodies are obtained which concurrently have a high strength or stability in longitudinal direction and a sufficient flexibility in lateral direction.

As only the matrix material of the central section is doped with marker particles, a particularly narrow and sharp artifact is generated in magnetic resonance imaging.

Such a concentrated arrangement of a lower amount of MR marker particles as compared to the state of the art is advantageous as a smaller number of blackened voxels results in the same degree of blackening, whereas the width of the blackened region is smaller as compared to the state of the art.

The width of the artifact of a rod-shaped body according to the present invention now is almost as narrow as for medical instruments known from the state of the art, particularly guidewires, which comprise at least one rod-shaped body because the MR marker particles due to the concentrated centric arrangement according to the present invention are already in the rod-shaped bodies sufficiently distant from the surrounding water or fat molecules, and not only in a guidewire with an envelope material which creates the sufficient distance to surrounding water or fat molecules. Thus the additional distance to surrounding water or fat molecules in the guidewires for example by providing an envelope material only adds a small but not a substantial additional advantage in the MR image.

Therefore, with a rod-shaped body with central doping according to the present invention it is possible to generate an artifact which is almost as narrow as with a guidewire.

The fiber bundles in the peripheral section according to this embodiment preferably are glass fibers.

It is also possible to use ceramic fibers instead of glass fibers.

The glass fiber bundles in the peripheral section provide the rod-shaped body with a very high compression and bending stiffness.

The aramid fiber bundles, which are arranged centrically on a neutral line, in contrast to the glass fiber bundles, which are only elastically deformable, are plastically deformable and nevertheless do not significantly reduce compression and bending stiffness of the rod-shaped body, but rather provide best possible tearing strength to it.

In this way a strongly improved rod-shaped body is provided which has best possible properties regarding compression and bending stiffness as well as tearing resistance.

The rod-shaped body 1 according to the present invention is manufactured in a micro-pultrusion process. Therein an aramid fiber bundle, or a roving, or a yarn, resp., together with a matrix material 4 doped with MR marker particles is centrically arranged and the central section 2 pultruded together with one or more glass fiber bundles and non-doped matrix material.

According to a second embodiment of the rod-shaped body all fiber bundles are ht-fiber bundles.

According to a third embodiment of the present invention the fiber bundle in the central section is a glass fiber bundle and in the peripheral section one or more ht-fiber bundles.

According to a fourth embodiment of the rod-shaped body all fiber bundles are provided as glass fiber bundles.

As described above the non-ferromagnetic matrix material in the central section and in the peripheral section is the same non-ferromagnetic matrix material with the sole difference that the matrix material in the central section 2 is doped with marker particles und in the peripheral section 3 the matrix material is non-doped. Preferably the matrix material is epoxy resin.

The MR marker particles are passive-negative MR markers, preferably selected from the following metals or metal compounds: iron (Fe), cobalt (Co), nickel (Ni), molybdenium (Mo), zirconium (Zr), titanium (Ti), manganese (Mn), rubidium (Rb), aluminum (Al), palladium (Pd), platinum (Pt), chromium (Cr) or chrome dioxide ($CrO_2$), or iron oxide (FeO, $Fe_2O_3$, $Fe_3O_4$).

The particle size of the passive-negative MR markers is in the range of 0 to 50 μm and in particular in the range of 0 to 20 μpm whereas the size indication relates to the smallest diameter. The concentration of the passive MR marker has to be chosen so that the medical instrument is visible with the desired sequences whereas they well visualize the medical instrument in at least one MR sequence but visualization of the surrounding body tissue concurrently is not significantly overlaid or affected. The weight/weight-ratio of MR markers and the matrix material of the central section is about 1:5 to 1:50, and in particular 1:10 to 1:20.

According to a second aspect of the present invention a guidewire 7 is provided which is formed preferably with one rod-shaped body. Such a guidewire can be a micro guidewire.

The rod-shaped body may be provided according to the above disclosed embodiments, yet preferably in the central section 2 an aramid fiber bundle is provided and in the peripheral section at least three glass fiber bundles are arranged. In the region of the distal end forming the tip of a guidewire the peripheral section is ground in such a way that the glass fiber bundles are removed to the largest extent, or almost completely, or completely, resp.

In that way a highly flexible and according to the requirements of the physician manually shapeable, i.e. by hand shapeable or deformable, distal tip is provided.

The micro guidewire preferably is enclosed by a PTFE shrink tube (Polytetrafluoroethylene). The shrink tube improves its properties regarding tearing strength and creates an optimally smooth surface with minimal friction which further optimizes the torque properties of the guidewire.

Figure 3:
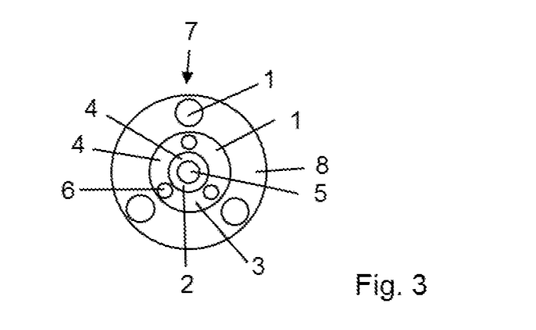

According to another aspect of the present invention a guidewire is provided which comprises several rod-shaped bodies 1 (FIG. 3).

The guidewire comprises a central rod-shaped body and at least three peripheral rod-shaped bodies whereas the central rod-shaped body is arranged in the center of the guidewire 7.

The peripheral rod-shaped bodies are radially arranged almost equally distant from each other around the central rod-shaped body.

The central rod-shaped body and the peripheral rod-shaped body extend substantially along the entire length of the guidewire. The rod-shaped bodies are embedded in a non-ferromagnetic matrix material.

According to the first embodiment of this guidewire the central rod-shaped body has a diameter of e.g. ca. 0.28 mm. Only aramid fiber bundles are provided as fiber bundles in the central rod-shaped body. These have a fineness of at least ca. 6 Tex, or at least ca. 22 Tex, and preferably of at least 11 Tex, whereas only the central aramid fiber bundle, arranged in the central section, is doped with MR marker particles. The aramid fiber bundles arranged in the peripheral section, however, are embedded in non-doped matrix material. The diameter of the central section is about 0.07 mm to 0.15 mm. The higher the value of fineness [Tex] is, the larger is also the diameter of the central section.

The peripheral rod-shaped bodies have a diameter of at least ca. 0.18 mm. These rod-shaped bodies are made from glass fiber bundles of a fineness of at least ca. 28 or at least ca. 33 Tex which are embedded in epoxy resin.

Such a guidewire comprises preferably one central rod-shaped body and three peripheral, or six peripheral, or three, or four, or five, or six, or seven, or eight, or nine, or ten, or eleven, or twelve, resp., peripheral rod-shaped bodies.

According to a second embodiment of the guidewire a central rod-shaped body according to the first embodiment of the guidewire is used, and the peripheral rod-shaped bodies have glass fiber bundles in the peripheral section with a fineness of at least ca. 28 or at least ca. 33 Tex and in the central section aramid fiber bundles which in the central section of the peripheral rod-shaped bodies are embedded in doped matrix material.

As an alternative to the two above described embodiments of guidewires, the central rod-shaped boxy may provide in the central section glass fibers which are embedded in a doped matrix material und whereas in the peripheral section aramid fiber bundles are embedded in non-doped matrix material.

Usually the glass fiber bundles in the rod-shaped bodies have a fineness of 5-100 Tex, and preferably 20-70 Tex. The diameter of the rod-shaped bodies preferably is between 0.1 mm and 0.4 mm.

Should one or more or all glass fiber bundles of a rod-shaped body break during the medical intervention the medical instruments nevertheless remain connected by the aramid fibers and, therefore, can be safely removed.

The rod-shaped bodies of this guidewire 7 are embedded in an envelope material. This e.g. can be biocompatible polymers such as polyamide, PEEK, PEBAX, polyethylene, polypropylene, polyurethane, EVA, PVP, PVC, silicone, polylactic acid polymers, Mediprene®, rubber materials or shape memory polymers.

The guidewire 7 preferably is enclosed by a PTFE shrink tube (Polytetrafluoroethylene). This improves its properties regarding the tearing strength and creates an optimally smooth surface with minimal friction which further optimizes the torque properties of the guidewire.

In another embodiment the envelope material is provided as modified compositions which primarily can be prepared by mechanical mixing. These chemical compositions provide one or more free functional groups, in particular amino and/or carboxyl groups. These chemical compositions comprise in particular polycarboxylic acids (e.g. polyacrylic acid, polyvinylamine, polyehtyleneimine, acrolein-acrylic acid-copolymer or polyallylamine). Especially preferable is a composition of an envelope material and polycarboxylic acid. In particular a sodium salt solution of polycarboxylic acid (e.g. POC AS 5060, Evonik Industries, Essen, Germany) is mixed with the envelope material, preferably to be obtained an amount of 5, 10, 20, 30 or 40, or more than 40% (w/w) POC in the envelope material. All amounts therebetween are also suitable and can be used. This modified envelope material then is used e.g. in an extrusion process in order to enclose and embed the rod-shaped bodies, or for coating of the ground flexible tip of a guidewire. The free carboxyl groups at the surface preferably react with polyamine or other polyamino polymers to result in amide bonds at the surface. Residual free amino groups then are preferably cross-linked with short-chain (e.g. $C_1$-$C_5$) hydrophilic alpha-omega homo-bifunctional linkers. The lubricious surface coating of the medical device in this way is stably fixed to the medical device. These modified surfaces are suitable for binding of passive-positive MR markers such as e.g. gadolinium ions or gadolinium complexes, or cerium, or praseodymium, or neodymium, or promethium, or samarium, or europium, or terbium, or dysprosium, or holmium, or erbium, or thulium, or ytterbium, or lutetium ions or complexes.

In the following the guidewires are categorized in predetermined classes exclusively according to their mechanical properties. The fiber content means the total fiber content of the respective rod-shaped body and is composed of one or more fiber bundles and may consist of one or more fiber types (e.g. ht-fiber or glass fiber). The guidewires contain each one single doped rod-shaped body according to the present invention. The other rod-shaped bodies preferably are non-doped. The doped rod-shaped body usually forms the central rod-shaped body of the guidewire as long as a central rod-shaped body is present.

1) Stiff or Super-Stiff Guidewire

A stiff of super-stiff guidewire typically has a diameter of 0.88 to 0.97 mm (0.035-0.038 inch). The central rod-shaped body has a fiber content of 40-80 Tex or higher, whereas it may be up to 100 Tex. At least 5, and in particular at least 6 or more peripheral rod-shaped bodies are provided. The fiber content of these rod-shaped bodies is in the range of 20 to 40 Tex. The envelope polymer may be provided as a medium or a hard polymer material. The softer the envelope polymer is, the stiffer are the rod-shaped bodies. Due to the peripheral arrangement of the peripheral rod-shaped bodies a slight increase in stiffness of the peripheral rod-shaped bodies results in a significant increase of the total stiffness of the guidewire. Therefore, the total stiffness of the guidewire can easily be adapted to the respective requirements by modifying the stiffness of the peripheral guidewires.

2) Standard Guidewire

A standard guidewire typically has a diameter in the range of 0.81 to 0.88 mm (0.032-0.035 inch). The central rod-shaped body has a fiber content of 40 to 80 Tex. The standard guidewire comprises two to four peripheral rod-shaped bodies. The peripheral rod-shaped body preferably has a fiber content of 20 to 40 Tex. The envelope polymer may be provided as a soft, a medium or a hard polymer material. The softer the envelope polymer is, the stiffer are the rod-shaped bodies. Due to the peripheral arrangement of the peripheral rod-shaped bodies a slight increase in stiffness of the peripheral rod-shaped bodies results in a significant increase of the total stiffness of the guidewire. Therefore, the total stiffness of the guidewire can easily be adapted to the respective requirements by modifying the stiffness of the peripheral guidewires.

3) Standard Micro Guidewire

A standard micro guidewire has a diameter of about 0.30 to 0.46 mm (0.012-0.018 inch). The central rod-shaped body has a fiber content of 20 to 70 Tex and in particular 40 to 60 Tex. The micro guidewire preferably comprises one to three peripheral rod-shaped bodies. The fiber content of the peripheral rod-shaped body preferably is about 10 to 30 Tex.

According to another embodiment of the standard micro guidewire it comprises only a single rod-shaped body with a fiber content of 70 to 130 Tex, and in particular 80 to 110 Tex. This rod-shaped body provides a passive-positive MR marker, such as e.g. iron particles. The concentration of the passive-positive MR marker in the matrix material is in the range of 1:5 to 1:30, and preferably in the range of 1:10 to 1:20. The particle size of the passive-positive MR marker particles is preferably 0 μm to 20 μm.

The envelope polymer may be provided as a soft, medium or hard polymer material. The softer the envelope polymer is, the stiffer are the rod-shaped bodies. Due to the peripheral arrangement of the peripheral rod-shaped bodies a slight increase in stiffness of the peripheral rod-shaped bodies results in a significant increase of the total stiffness of the guidewire. Therefore, the total stiffness of the guidewire can easily be adapted to the respective requirements by modifying the stiffness of the peripheral guidewires.

4) Flexible Micro Guidewire

A flexible micro guidewire has a diameter of about 0.20 to 0.25 mm (0.008-0.010 inch). It has only one central rod-shaped body. The central rod-shaped body preferably has a fiber content of 40 to 80 Tex. The envelope polymer may be provided as a soft or medium-hard polymer material.

In the following a method for manufacturing of a rod-shaped body according to the present invention is described.

According to this further aspect of the present invention a central section of at least one non-metallic fiber bundle with a non-ferromagnetic matrix material doped with MR marker particles is provided, and on the central section by impregnation of at least one non-metallic fiber bundle with undoped non-ferromagnetic matrix material a peripheral section is provided so that the latter encloses the central section. In this way the rod-shaped body is provided.

Concerning the features of the invention not illustrated in detail in the above disclosure it is further expressly referred to patent claims and the drawings.

LISTS OF REFERENCE NUMERALS

1 Rod
2 Central section
3 Peripheral section
4 Non-ferromagnetic matrix material
5 Non-metallic fiber bundle
6 Non-metallic fiber bundle
7 Guidewire
8 Envelope polymer

The invention claimed is:

1. A rod-shaped body, comprising
a central section and a peripheral section, wherein the central section is arranged in the center of the rod-shaped body and enclosed by the peripheral section, wherein the central section as well as the peripheral section substantially extend along the entire length of the rod-shaped body, and the central section comprises at least one non-metallic fiber bundle embedded in a non-ferromagnetic matrix material, wherein only the matrix material of the central section is doped with MR marker particles, and the peripheral section provides an undoped, non-ferromagnetic matrix material, wherein the diameter of the central section is less than or equal to 0.2 mm.

2. The rod-shaped body according to claim 1, characterized in that the matrix material of the peripheral section or of the entire rod-shaped body is a homogeneous matrix material.

3. The rod-shaped body according to claim 1, characterized in that a non-metallic fiber bundle is embedded in the undoped, non-ferromagnetic matrix material of the peripheral section.

4. The rod-shaped body according to claim 3, characterized in that in the peripheral section the non-metallic fibers are arranged about equally distributed relative to the cross-section.

5. The rod-shaped body according to claim 1, characterized in that the diameter of the central section is less than or equal to 0.15 mm.

6. The rod-shaped body according to claim 1, characterized in that the fiber bundle comprises at least one elongated or several elongated fibers.

7. The rod-shaped body according to claim 3, characterized in that the fiber bundle in the central section is an ht-fiber bundle and in the peripheral section is a glass fiber bundle.

8. The rod-shaped body according to claim 1, characterized in that all fiber bundles are ht-fiber bundles.

9. The rod-shaped body according to claim 3, characterized in that the fiber bundle in the central section is a glass fiber bundle and in the peripheral section is an ht-fiber bundle.

10. The rod-shaped body according to claim 1, characterized in that the central section and the peripheral section of the rod-shaped body each are provided with the same non-ferromagnetic matrix material.

11. The rod-shaped body according to claim 3, characterized in that in the central section are provided one or two fiber bundles and in the peripheral section three to eight fiber bundles.

12. A medical instrument comprising
at least one rod-shaped body according to claim 1, wherein the at least one rod-shaped body extends substantially along the entire length of the medical instrument, and wherein the rod-shaped body comprises at least one non-metallic fiber bundle embedded in a non-ferromagnetic matrix material.

13. The medical instrument according to claim 12, characterized in that at a distal end region of the medical instrument an MR tip marker is provided.

14. The medical instrument according to claim 12, wherein the medical instrument is a guidewire and the at least one rod-shaped body is embedded in a non-ferromagnetic envelope material.

15. A guidewire,
comprising one central rod-shaped body according to claim 1 and at least one peripheral rod-shaped body, wherein the central rod-shaped body is arranged in the center of the guidewire, and wherein the central rod-shaped body and the peripheral rod-shaped body extend substantially along the entire length of the guidewire, and the central rod-shaped body and the peripheral rod-shaped body are embedded in a non-ferromagnetic envelope material, wherein the peripheral rod-shaped body provides at least one non-metallic fiber bundle embedded in an undoped, non-ferromagnetic matrix material.

16. The guidewire according to claim 15, wherein the central rod-shaped body is characterized by at least one of the following characteristics (i)-(iii):
(i) in the peripheral section the non-metallic fibers are arranged about equally distributed relative to the cross-section;
(ii) the diameter of the central section is less than or equal to 0.15 mm; and
(iii) the fiber bundle comprises at least one elongated or several elongated fibers, and wherein the fiber bundle(s) of the at least one peripheral rod-shaped body are glass fiber bundles.

17. The guidewire according to claim 15, characterized in that one central rod-shaped body and three to eight peripheral rod-shaped bodies are provided.

18. The guidewire according to claim 15, characterized in that in the region of the distal end forming the tip of a guidewire the amount of glass fibers is smaller than in the other part of the guidewire.

19. A method for manufacturing a rod-shaped body according to claim 1,
wherein a central section of at least one non-metallic fiber bundle with a non-ferromagnetic matrix material doped with MR marker particles is provided, and on the central section by impregnation of at least one non-metallic fiber bundle with undoped non-ferromagnetic matrix material a peripheral section is provided so that the latter encloses the central section.

* * * * *

UNITED STATES PATENT AND TRADEMARK OFFICE
CERTIFICATE OF CORRECTION

PATENT NO. : 10,758,316 B2
APPLICATION NO. : 15/306088
DATED : September 1, 2020
INVENTOR(S) : Klaus Düring Page 1 of 1

It is certified that error appears in the above-identified patent and that said Letters Patent is hereby corrected as shown below:

On the Title Page

Item (30) Foreign Application Priority Data:
"(DE).............10 2014 005 777" should be -- 10 2014 005 777.1 --.
"(DE).............10 2014 005 994" should be -- 10 2014 005 994.4 --.

In the Specification

Column 3, Line 62 "pm to some mm" should be -- µm to some mm --.

Column 11, Line 61 "0 to 20 µpm" should be -- 0 to 20 µm --.

Signed and Sealed this
Twentieth Day of October, 2020

Andrei Iancu
*Director of the United States Patent and Trademark Office*